United States Patent [19]

Rich et al.

[11] Patent Number: 5,726,050
[45] Date of Patent: Mar. 10, 1998

[54] Z-DNA BINDING PROTEIN AND APPLICATIONS

[75] Inventors: Alexander Rich, Cambridge; Alan Herbert, Belmont, both of Mass.

[73] Assignee: Massachusetts Institute of Technology, Cambridge, Mass.

[21] Appl. No.: 492,599

[22] Filed: Jun. 20, 1995

[51] Int. Cl.$^6$ .......................... C12N 15/85; C12N 15/63; C12N 15/62; C12N 5/10
[52] U.S. Cl. .......................... 435/172.3; 435/6; 435/7.21; 435/69.1; 435/69.7; 435/91.4; 435/172.1; 435/196; 435/212; 435/320.1; 435/375; 536/23.1; 536/23.2; 536/23.4; 536/23.5; 536/24.1; 514/44
[58] Field of Search .......................... 435/6, 7.21, 69.1, 435/69.7, 91.4, 196, 212, 172.3, 240.2, 320.1, 375; 514/44; 536/23.1, 23.2, 23.4, 23.5, 24.1

[56] References Cited

PUBLICATIONS

D. Brown, Washington Post, Friday, Dec. 8, 1995 pp. A1, A22.
A. Coghlan New Scientist Nov. 25, 1995 pp. 14–15.
Schroth et al., *J. Biol. Chem.* 267: 11846 (1992).
Liu and Wang, *Proc. Natl. Acad. Sci. USA* 84: 7024 (1987).
Wittig et al., *EMBO J.* 11: 4653 (1992).
Herbert and Rich, *Nucleic Acids Research* 21: 2669 (1993).
Möller et al., *Biochemistry* 23: 54 (1984).
Haniford and Pulleyblank, *J. Biomolecular Structure and Dynamics* 1: 593 (1983).
Kim et al., *Proc. Natl. Acad. Sci. USA* 91: 11457 (1994).
O'Connell et al., *Molec. & Cell. Biol.* 15: 1389 (1995).

*Primary Examiner*—Charles C. P. Rories
*Attorney, Agent, or Firm*—Kevin M. Farrell

[57] ABSTRACT

Disclosed is the isolation of a 140,000 kDa protein which binds with high affinity to Z-DNA. Z-DNA is defined herein as a non-B-DNA conformer which is stabilized by negative supercoiling. The isolated protein also has a binding site for double-stranded RNA (dsRNA). Peptide sequences from this protein show similarity to double-stranded RNA adenosine deaminase (dsrad), an enzyme which deaminates adenosine in dsRNA to form inosine. Assays for this enzyme confirm that dsrad activity and Z-DNA binding are properties of the same molecule. The coupling of these two activities in a single molecule indicate a novel mechanism of gene regulation which is in part dependent on DNA topology.

26 Claims, 2 Drawing Sheets

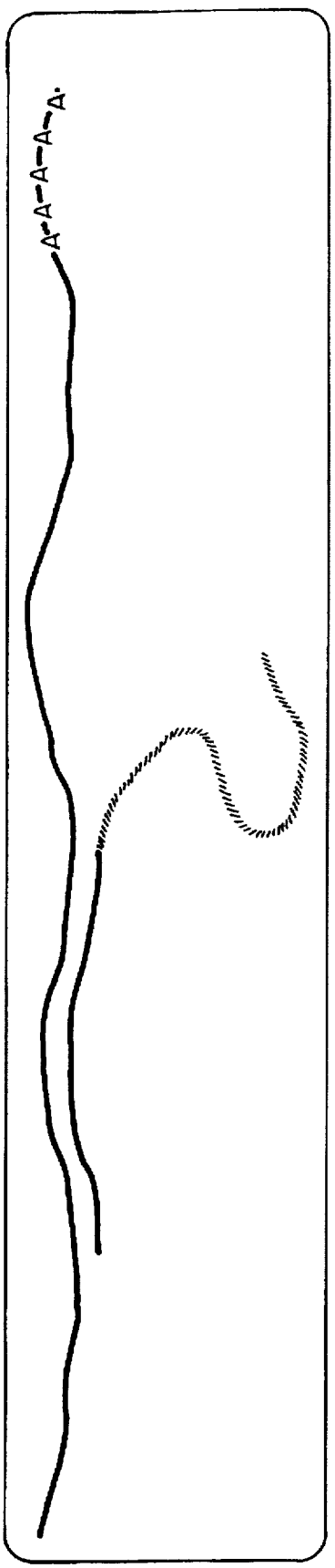
FIG. IA
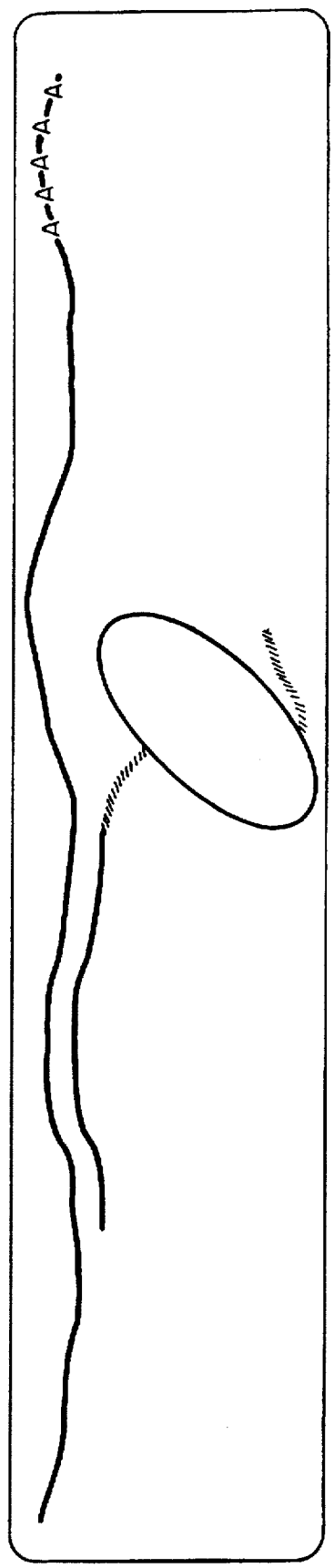
FIG. IB

5,726,050

Z-DNA BINDING PROTEIN AND APPLICATIONS

GOVERNMENT SUPPORT

Experimental work described herein was supported by grants from the United States Government which may have certain rights in the invention.

BACKGROUND OF THE INVENTION

It is currently unclear what role(s) Z-DNA plays inside a cell. Since its crystallographic description in 1979, there have been many proposals concerning the function of this left-handed DNA conformer in biological processes. Many experiments designed to address these proposals have been confounded by experimental artifacts. Consequently, no consensus as to the biological relevance of Z-DNA has yet emerged. Z-DNA is formed best in vitro by sequences of alternating deoxycytosine and deoxyguanosine and poorly by alternating deoxyadenosine and thymine. The structure can be stabilized in covalently closed plasmids by negative supercoiling: underwound regions of a plasmid relax when a segment of DNA adopts a reverse twist. The amount of negative supercoiling necessary to push a sequence into the Z-DNA conformer has been used to rank the ease with which particular sequences form this structure. These empirical rankings can be modeled computationally using statistical mechanical techniques. When applied to analysis of 137 human gene sequences, one such study showed that potential Z-DNA forming sequences are located non-randomly within genes (Schroth et al., (1992) *J. Biol. Chem.* 267, 11846–11855). They are present more often at the 5' end of a gene (~35%) than at the 3' end (~3%) and often in promoter regions. Only 15% of Z-DNA forming elements are found in exons while nearly half (47%) are found in introns.

In vivo, the negative supercoiling necessary to initiate Z-DNA may arise from transcription. According to the two domain model of Liu and Wang (Liu and Wang, (1987) *Proc. Natl. Acad. Sci. USA* 84: 7024–7027), the transcription complex containing RNA polymerase ploughs through a gene, leaving in its wake underwound DNA. The sequence 5' to the transcription complex becomes negatively supercoiled, storing the energy generated by the machinery of transcription. This energy is available to promote formation of Z-DNA. Indeed, formation of Z-DNA in the 5' part of the c-myc gene during transcription has been observed experimentally by probing metabolically active human nuclei embedded in agarose microbeads with an anti-Z-DNA monoclonal antibody.

Thus, the evidence suggests a transcriptional regulatory role for Z-DNA. Prior to the work described herein, insight into this regulatory mechanism was not sufficiently understood to facilitate intervention and the development of methods for the modification of gene expression.

SUMMARY OF THE INVENTION

In one aspect, the present invention relates to expressible genetic constructs and fusion proteins encoded by such constructs. A common element to each of the fusion proteins is the presence of a Z-DNA binding protein, or a portion thereof which retains Z-DNA binding specificity. In one embodiment, this Z-DNA binding domain is linked to an effector function. A second embodiment includes the elements of the first embodiment and, in addition, a B-DNA binding domain which is characterized by the ability to bind to a transcribed region of a gene of interest. A third embodiment includes the Z-DNA binding domain and a B-DNA binding domain from a protein, the binding of said protein to a specific site in genomic DNA functioning to enhance transcription. Each of these embodiments are useful in connection with methods for modifying gene expression.

In another aspect, the invention relates to a bivalent therapeutic reagent which, when present in the nucleus of a cell, functions to recruit an mRNA editing enzyme to a site of active transcription. In addition, a portion of the bivalent reagent binds specifically to a portion of a nascent mRNA thereby forming a substrate for the mRNA editing enzyme. By careful selection of the portion of the reagent which binds specifically to the mRNA, specific base changes can be introduced in the mRNA which can alter aspects of expression such as translation initiation sites, mRNA splice sites, reading frame shifts, introduction of stop codons, etc. In some cells, the editing enzyme may accumulate in the cytoplasm. This can occur, for example, during one phase of the cell cycle. This accumulation would allow cytoplasmic modification of RNA by the therapeutic reagent.

DETAILED DESCRIPTION OF THE INVENTION

Figure 1C:
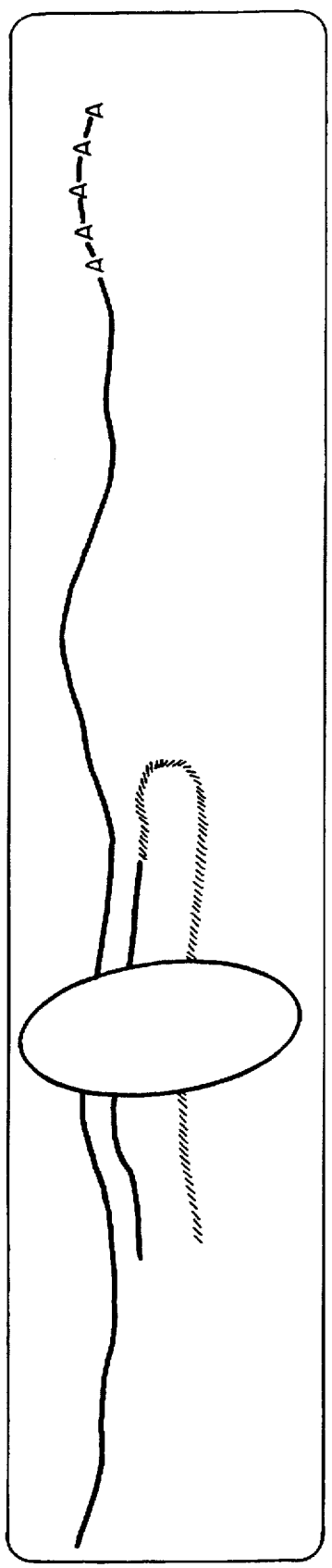
FIGS. 1(A–C) is a diagram representing the therapeutic reagent of the present invention binding to a mRNA molecule in the presence of an enzyme having a Z-DNA binding domain and a double-stranded RNA editing domain.

The present invention is based on the isolation of a 140,000 kDa protein which binds with high affinity to Z-DNA. Z-DNA is defined herein as a non-B-DNA conformer which is stabilized by negative supercoiling. The isolated protein also has a binding site for double-stranded RNA (dsRNA). Peptide sequences from this protein show similarity to double-stranded RNA adenosine deaminase (dsrad), an enzyme which deaminates adenosine in dsRNA to form inosine. Assays for this enzyme confirm that dsrad activity and Z-DNA binding are properties of the same molecule. The coupling of these two activities in a single molecule indicate a novel mechanism of gene regulation which is in part dependent on DNA topology.

The newly identified Z-DNA binding domain can be exploited in a variety of applications. Z-DNA forming sequences are located non-randomly within genes (Schroth et al., (1992) J. Biol. Chem. 267, 11846–11855). More specifically, it has been reported that Z-DNA is found more often at the 5' end of a gene (particularly in a promoter region), than at the 3' end of a gene. Transcription is associated with increased Z-DNA formation, largely in the upstream region (Wittig et al., (1992) *EMBO J.* 11, 4653–4663). Thus, the newly identified Z-DNA binding domain can be used as a targeting domain for the delivery of a second functional domain to regions of active gene transcription. By linking the Z-DNA binding domain to a second functional domain, the second functional domain is delivered to a site of active transcription, thereby increasing the local concentration of the second functional domain in the area of active transcription. As discussed in greater detail below, the second functional domain can be selected based on the ability to disrupt transcription. Thus, in one aspect, the present invention relates to fusion proteins and methods which can be used to modify gene expression. As used herein, the word "modify" includes, for example, both inhibition and activation of gene expression.

The Z-DNA binding protein can be any of the Z-DNA binding proteins specifically discussed in the Exemplification section set forth below. These include the newly isolated 140,000 kDa protein which demonstrates homology to dsrad. In addition, this includes dsrad isolated from any other metazoan source. Such additional dsrad isolates can be isolated, for example, by probing cDNA libraries from a metazoan source with a DNA probe corresponding to the published human or rat dsrad sequences (Kim et al., (1994) *Proc. Natl. Acad. Sci. USA* 91, 11457–11461; O'Connell et al., (1995) *Mol. Cell. Biol.* 15, 1389–1897). Alternatively, an affinity purification scheme designed to exploit the presence of the two binding specificities (Z-DNA and double-stranded RNA) can be employed to isolate dsrad family members. For example, two column steps could be employed in such an isolation scheme: a first column containing Z-DNA fixed to a solid support, and second column containing double-stranded RNA fixed to a solid support. Cell lysates can be passed over the first column and material retained can be eluted, then passed over the second column. Material eluting from the second column should be characterized by the presence of the two dsrad binding specificities. Peptide sequence obtained from proteins isolated in this manner can then be used to design oligonucleotide probes useful for identifying the corresponding gene in a cDNA library. Not all embodiments require the mRNA editing function of dsrad. For those embodiments which do not require this function, proteins which bind Z-DNA can be isolated using only the first column step specified in the preceding paragraph. In addition, new Z-DNA binding proteins useful in connection with the present invention can be isolated using no more than routine experimentation through the use of a band-shift assay. In this assay, an oligomer of alternating deoxycytosine and deoxyguanosine can be employed. The oligomers are modified by using the Klenow fragment of *E. coli* DNA polymerase I to incorporate a $^{32}P$ labeled dGTP and d5BrCTP (Herbert and Rich, (1993) *Nucleic Acids Res.* 21, 2669–2672). In addition, other Z-DNA forming sequences such as alternating deoxyguanosine and deoxythymidine can be employed in a band-shift assay. Binding specificity of proteins is then determined by competition experiments using unlabeled DNA or RNA. As indicated in the Exemplification section which follows, Z-DNA specific interactions were demonstrated using either linear brominated polyd(CG) (Moller et al., (1984) *Biochemistry* 23, 54–62), or the plasmid pDHg16 which has a d(CG)13 insert in the Z-DNA conformation at bacterial superhelical density (Herbert and Rich, (1993) *Nucleic Acids Res.* 21, 2669–2672; Haniford and Pulleyblank, (1983) *J. Biomol. Struct. Dyn.* 1, 593–609).

Fusion proteins which are useful in connection with the modification of gene expression are most conveniently constructed using conventional recombinant DNA techniques (see e.g., Sambrook et al., (1989) *Molecular Cloning: A Laboratory Manual* (Cold Spring Harbour Lab., Plainview, N.Y.), 2nd Ed.). The arrangement of the fusion elements in the individual fusion proteins of the present invention does not appear to be critical based on any experimental evidence. As discussed above, the DNA sequence of certain dsrad proteins has been published. Methods are described herein which facilitate the identification of additional dsrad proteins (or, when appropriate, Z-DNA binding proteins which do not necessarily belong to the dsrad family), and the isolation of the cDNA encoding them.

DNA encoding an entire Z-DNA binding protein can be used as a component of such fusion proteins, or alternatively, only the required functional domain(s) need be included. For example, in specific embodiments of the present invention, only the Z-DNA binding domain of a Z-DNA binding protein (e.g., a dsrad protein) is required. To identify the minimum number of amino acids required to form a functional Z-DNA binding domain, the entire Z-DNA binding protein can be digested with an endoprotease to generate specific protein fragments. These fragments can be isolated, and tested individually for the ability to bind Z-DNA. The band-shift assay described elsewhere in the present application could be used to detect specific binding of a proteolytic fragment to Z-DNA. Using this technique, the Z-DNA binding region has been localized to the first 500 amino acids of human dsrad.

Thus, in one embodiment, DNA encoding a Z-DNA binding protein, or a portion thereof which retains Z-DNA binding specificity, is fused in frame to an effector function. The fusion protein encoded by the expression construct is characterized by the ability to selectively modify gene expression. Although considerations relevant to the selection of an effector function for use in connection with the present embodiment will be discussed in greater detail below, a general discussion of effector function will be provided at this point.

As used herein, the expression "effector function" refers to an enzymatic activity or binding activity which can function to modify gene expression. Among the many examples of such enzymatic activities are: nuclease activity, protease activity, protein modifying activity and mRNA editing activities.

Nuclease activity includes both RNAase and DNAase activity. Many examples of enzymes possessing an RNAase activity or a DNAase activity have been reported in the literature (see e.g., *Nucleases*, Linn et al. Eds. 2nd ed. (1993) Cold Spring Harbor Laboratory Press). The use of a nuclease activity as an effector domain is based on the recognition that the Z-DNA binding domain in the fusion protein will target the fusion protein to regions of active transcription thereby increasing the local concentration of the effector domain. If, for example, the effector domain is an RNAase (e.g., Ribonuclease A, Ribonuclease T1, Ribonuclease T2, etc.) the result of increasing the local concentration of an RNAase in an area of active transcription is to promote digestion of nascent mRNA thereby inhibiting the expression of the gene being transcribed.

With respect to protease activities, the literature is replete with reports concerning proteins which exhibit such activities. Many of these reports include nucleic acid sequence information which would be useful in connection with the design of an expression construct. Where, on the other hand, all that is disclosed is a method for isolating a given protease, the isolation of cDNA encoding the protease is a matter of routine experimentation. Steps which would be followed to isolate the cDNA are outlined elsewhere in the Specification. The effect of localizing a protease activity in an area of active transcription is to promote the digestion of proteins in the area which may be required for gene expression (including, for example, RNA polymerase, transcription activating factors, etc.). It should be noted that the use of a carefully selected protease activity as an effector domain may serve to fine tune the targeting of the fusion protein beyond the targeting information provided by the Z-DNA binding domain. The degree of refinement, however, does not approach that provided by the protein modifying activities and mRNA editing activities discussed below.

Protein modifying activities include, for example, phosphorylative or dephosphorylative activities (Kurosawa, *J. Pharmacol. Toxicol. Methods* 31(3), (1994) 135–9). It is known, for example, that certain proteins are active only when specifically phosphorylated or dephosphorylated. The ability to specifically phosphorylate or dephosphorylate proteins in an area of active transcription affords the opportunity to modify gene expression by either phosphorylating or dephosphorylating a protein which plays a role in transcription, thereby modifying gene expression. Since the number of proteins whose activity would be affected by such modification is small, relative to the total number of proteins likely to participate in the regulation of transcription in the local area targeted by the Z-DNA binding domain, the use of such effector functions can fine tune the targeting of the fusion protein thereby substantially reducing the number of actual targets.

With regard to mRNA editing activities, there are three types of mRNA editing that have been described in the literature (Bass in *The RNA World*, (1993) Gesteland and Atkins, Eds. (Cold Spring Harbour Laboratory Press, Long Island, N.Y.). Addition/deletion editing is used by protozoans and its evolutionary consequences are well recognized. Substitution editing of RNA (SE), where one base is replaced by another, is a more general process and takes two forms. One type of SE require a specific single-stranded RNA sequence on which to act and requires the evolution of appropriate sequence-specific proteins. The other form requires a double-stranded RNA template (dsRNA). In connection with the present invention, it is the mRNA editing function which requires a double-stranded RNA template which is most relevant. Depending on the particular embodiment of the present invention being discussed, either a single-stranded RNA editing enzyme or a double-stranded RNA editing enzyme may be appropriate. For example, the single-stranded RNA editing enzyme may be appropriate for use as an effector domain of a fusion protein. When localized to an area of active transcription, a single-strand specific mRNA editing enzyme (e.g., cytosine deaminase) can introduce a change which can modify gene expression. In particular, the editing function of cytosine deaminase can function to introduce stop codons where such codons were not previously found. As discussed more fully below, a double-stranded RNA editing enzyme is appropriate for use in connection with the use of an antisense construct.

A review of the literature relating to the myriad of enzymatic activities which could function as an effector domain in connection with the present invention is beyond the scope of this discussion. One of skill in the art, based on the teaching of the specification, will be able to select from among the many potential effector domains, a domain which is appropriate to disrupt the expression of a particular gene of interest.

As mentioned briefly above, the fusion protein of the present embodiment is characterized by the ability to selectively modify gene expression. "Selectively", as used in this context, implies a targeting specificity beyond that provided by the Z-DNA binding domain (which targets the fusion protein to genomic DNA which is actively transcribed in any cell in which the fusion is introduced). Several effector functions which confer upon the fusion protein a degree of specificity beyond that provided by the Z-DNA binding domain have been discussed above. The use of effector functions which do not further refine the target specificity of the fusion protein beyond that provided by the Z-DNA binding domain are not prohibited, however. For example, if the expression construct is placed under the control of a tissue-specific promoter, a more generally effective effector function can be employed and its influence (typically cell death due to the non-selectivity of action in a cell in which it is expressed) will be confined to cells in which the particular promoter selected is active.

For example, if it is desirable to specifically kill cells which are infected by a retrovirus (e.g., HIV-I), the expression construct can be placed under the control of a retroviral promoter. Under the control of this promoter, the expression construct will only be expressed in cells which are infected by the retrovirus.

In another embodiment of the present invention the Z-DNA binding domain and an effector function (which need not necessarily refine the targeting specificity provided by the Z-DNA binding domain), are combined with DNA encoding a B-DNA binding domain. The B-DNA binding domain is derived from a protein which binds to a specific site in genomic DNA thereby activating or enhancing transcription of a gene of interest. Such proteins are referred to herein as "activators" of transcription. Most, if not all eukaryotic protein-coding genes require activators for efficient expression. In simple eukaryotic systems such as yeast, the specific binding of an activator to a single upstream activating sequence (UAS) can be sufficient for enhanced transcription. Such sequences are typically located near the gene.

Mammalian genes, on the other hand, typically contain multiple protein binding sites. The binding of a specific activator to each of these sites is necessary for maximal transcription levels. In some cases, such gene-activating sites are located great distances (e.g., up to 50 kb) from the site of transcription initiation. These sites are typically upstream of the gene of interest, but sometimes are found downstream. These remote activating sites were originally referred to as enhancer-sequences. Other gene-activating sites, such as promoter sequences, are known to be at or near the transcription start site. In addition, gene-activating sites can be located at virtually any other location within genomic DNA including, for example, within intron or exon sequences and within the 3' non-coding region of a gene.

A variety of site-specific B-DNA binding proteins have been reported in the literature (see e.g., Johnson and McKnight, (1989) *Ann. Rev. Biochem.*, 58: 799; and Murre et al., (1989) *Cell* 56: 777). In addition, it is a matter of routine experimentation to isolate such B-DNA binding proteins. For example, to isolate a B-DNA binding protein which binds specifically to a particular gene, genomic DNA containing the gene can be fixed to a solid support and an affinity column can be generated using this material. A cell lysate is passed over the affinity column and proteins which specifically bind to the B-DNA are retained, and subsequently eluted. If multiple proteins elute from the column, it is likely that they represent proteins binding to distinct sites in the B-DNA, and this mixture of specific-binding proteins can be purified from one another by conventional techniques.

Amino acid sequence information can be obtained, for example, by digesting purified protein with an endoprotease and determining the amino acid sequence of peptides generated by digestion. The amino acid sequence determined in this manner can be compared with sequences of record in databases such as the EMBL or GENBANK databases. If a match is determined, the DNA sequence encoding the isolated protein is downloaded from the database. If no match is determined, a degenerative oligonucleotide set can be designed and prepared by conventional techniques and used to screen a cDNA library.

An expression construct is then synthesized by linking DNA encoding Z-DNA and a B-DNA binding protein. The fusion protein encoded by this construct is specifically targeted to regions of active transcription by the Z-DNA element, thereby increasing the local concentration of the fusion protein to regions of genomic DNA which are actively transcribed. Since the binding site for transcription activator proteins is preferably also located in or near an actively transcribed region, the Z-DNA portion increases the rate at which the B-DNA binding domain recognizes and binds to its target sequence. The B-DNA binding domain is characterized by the ability to bind specifically, and with high affinity to the specific site in genomic DNA, and further by the inability to enhance transcription of the gene of interest. Thus, in essence, the B-DNA binding domain is rendered defective in its transcription activation function. It binds with high affinity to the transcription activation site and, in doing so, prevents binding to the same site by the intact transcription activator.

In an alternative embodiment, a fusion protein comprising a Z-DNA binding domain and non-defective activator of transcription can be used to enhance transcription of a gene of interest. Linking Z-DNA to the activator protein functions to increase the local concentration of the activator protein in an actively transcribed region.

The fusion proteins described above can be introduced into cells either by transfecting the cells with the DNA comprising the expression construct, or by contacting the cells with the fusion protein encoded by the expression construct under conditions appropriate for uptake of the fusion protein by the cell. The introduction of DNA into a cell by transfection is a routine procedure to those skilled in the art (see e.g., Sambrook et al., (1989) *Molecular Cloning: A Laboratory Manual* (Cold Spring Harbour Lab., Plainview, N.Y.), 2nd Ed.). Several types of vectors appropriate for the present application are already available (reviewed by Yee et al., *Proc. Natl. Acad. Sci. USA* 91: 9564 (1994); see also Mulligan, *Science* 260: 926 (1993) and Anderson, *Science* 256: 808 (1992)). These vectors can be used for the delivery of fusion proteins in cell cultures, in whole animals, and, with appropriate preliminary testing, in human patients as well. Recent advances in the design of viral and plasmid-based vectors (see e.g., Nabel et al., *Proc. Natl. Acad. Sci. USA* 90: 11307 (1993) and Mulligan, *Science* 260: 926 (1993)) resulted in tailor-made, nonreplicating vectors that can transfect both growing and quiescent cells, and are either specific for cells that bear a predetermined surface marker or almost nonselective. Such vectors, in use for gene therapy and other applications (for example, Mulligan, *Science* 260: 926 (1993) and Anderson, *Science* 256: 808 (1992)), are powerful vehicles for the delivery of the compositions of the present invention.

A variety of techniques are currently under development which would enable the introduction of an expressed fusion protein into a cell. A number of these techniques exploit the existence of certain cell membrane receptors which mediate the uptake of extracellular materials. It has been demonstrated, for example, that by chemically attaching folate moieties to the surface of a protein, the coated protein can interact with the folate receptor on the surface of a cell which mediates the uptake of the folate-coated protein by the cell (Turek et al., (1993) *J. Cell. Sci.* 106, 423). Thus, a folate-coated fusion protein can be introduced into the plasma of an individual, and interaction with the folate receptor will mediate cellular uptake. In addition to such receptor-based methodologies, proteins can be introduced into cells by encapsulating the proteins in liposomes (Hnatyszyn et al., (1994) *PDA J. Pharm. Sci. Technol.* 48: 247).

A required element of the fusion proteins (and, therefore, the expression constructs encoding the fusion proteins) is a nuclear localization signal (NLS). Proteins smaller than ~60 kD can enter the nucleus by diffusing through the nuclear pores, but the pore-mediated transport of a larger protein requires the presence of at least one NLS accessible to components of the nuclear translocation system. NLSs are short sequences (10-20 residues) rich in lysine and arginine; their steric accessibility in a target protein appears to be sufficient for their activity as nuclear translocation signals. NLS-bearing proteins enter the nucleus shortly after their synthesis in the cytosol.

In addition to the embodiments described above which relate to expression constructs and fusion proteins encoded by the expression constructs, the present invention also relates to antisense technology. More specifically, it has been demonstrated that the dsrad family of proteins possess a Z-DNA binding function and a double-stranded mRNA editing function. This enzyme deaminates adenosine in regions of double-stranded RNA to form inosine. This leads to destabilization of RNA secondary structure since basepairs are replaced by I-U basepairs, and also to changes in translation of mRNA because inosine is read as guanosine. The changes made by dsrad are of major biological significance as they alter the flow of information from DNA to mRNA.

More specifically, a change from A to I, which is translated as G, may cause changes in the properties of a protein by exchanging one amino acid for another and is identified by comparing genomic and cDNA sequences (Bass in *The RNA World*, (1993) Gesteland and Atkins, Eds. (Cold Spring Harbour Laboratory Press, Long Island, N.Y.)). In addition, in light of the fact that adenosine is used in either the branch site or the acceptor site in mRNA splicing reactions, conversion to guanosine causes an alteration of splicing patterns, causing changes within a protein. The alteration of an initiation codon from AUG to GUG alters the N-terminus of a protein. Alternatively this may result in use of a different reading frame. Alteration of the stop codons UGA, UAA or UAG stop codons by conversion of A to G would result in the stop codon being read as encoding tryptophan (UGG) which would result in the alteration of the C-terminus of a protein. In addition, substituting I-U basepairs for A-U basepairs would be predicted to alter the susceptibility of pre-mRNA to nucleases.

The presence in cells of an enzyme having the dual functionality of dsrad can be exploited in a therapeutically beneficial manner. Specifically, a therapeutic reagent can be designed which recruits an enzyme having the dual dsrad functionality. As shown in FIG. 1, the components of the therapeutic reagent are: 1) an oligonucleotide comprising Z-DNA (non-solid line), linked to an RNA molecule (solid line) which is complementary to a selected region in a mRNA molecule of interest (solid line with poly(A) tail). Linkage is of sufficient length so that each element of the therapeutic reagent can be bound by the enzyme in a manner that allows editing to occur and of sufficient stability to give the therapeutic a sufficient biological half-life. An example of an appropriate linker sequence is an aliphatic carbon chain synthesized by conventional techniques using commercially available reagents designed for the chemical synthesis of nucleic acids. The selected region of the mRNA of interest must contain an adenosine group or another nucleoside substrate of an RNA editing enzyme. The RNA molecule which is complementary to the selected region in the mRNA molecule should be long enough to form a stable hybrid complex (e.g., at least about 15 nucleotides in length)

as shown in panels B and C of FIG. 1, and must also be long enough to form a double-stranded RNA complex which is recognized and acted upon by the enzyme having the double-stranded mRNA editing function (e.g., dsrad) (depicted as an oval in FIG. 1).

Using conventional recombinant DNA techniques, an expression construct is prepared which encodes the bivalent nucleic acid construct described in the preceding paragraph. This construct is introduced into cells by transfection techniques as described previously. Following transcription in the cell by RNA polymerase I, II or III, the RNA portion of the reagent specifically binds to the mRNA at the predetermined location (FIG. 1, panel B). The construct also contains, near the transcribed region, sequences that can form Z-DNA as a result of transcription. The ease with which these sequences can form Z-DNA can be varied to optimize the degree of modification of the RNA. An enzyme having both a Z-DNA binding function and a double-stranded RNA editing function (oval in FIG. 1) is recruited based on its affinity for Z-DNA (non-solid line in FIG. 1), thereby increasing the local concentration of the enzyme.

Figure 2A:
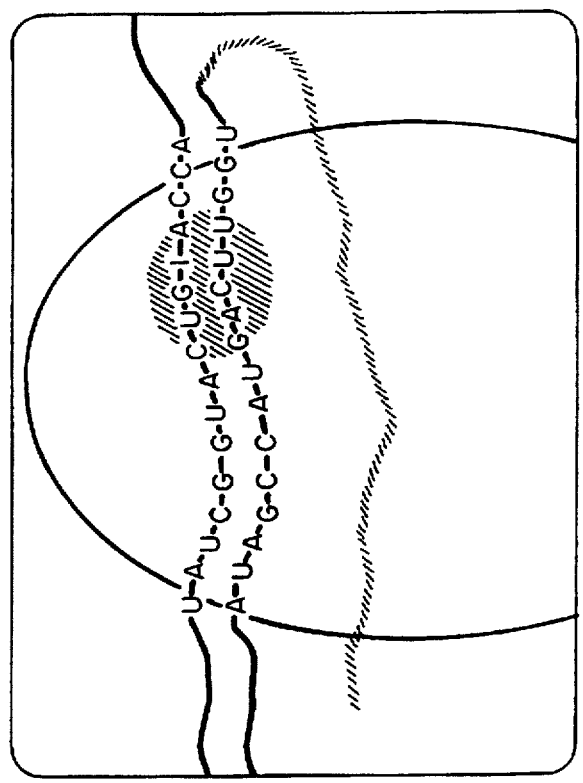
FIGS. 2(A and B) is a diagram representing the conversion of a stop codon to a tryptophan-encoding codon by mRNA editing.
Figure 2B:
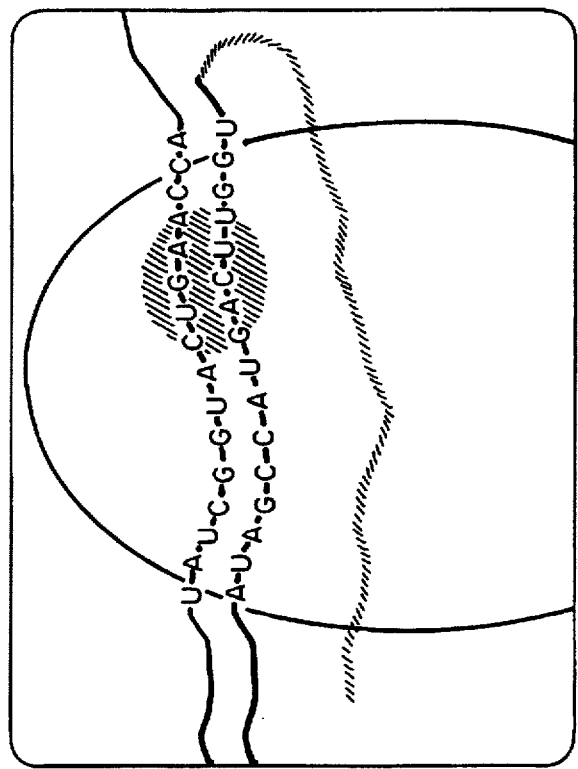

The double-stranded RNA formed between the mRNA and the RNA portion of the therapeutic reagent is recognized by the enzyme as shown in FIG. 2. In FIG. 2, the large oval again represents the bivalent protein (for example, dsrad). The solid upper line represents mRNA and the line having both a solid portion and a non-solid portion represents the therapeutic reagent of the present invention. The shaded oval represents the site of double-stranded mRNA editing on the bivalent protein. Prior to mRNA editing, the mRNA depicted in FIG. 2 contains a stop codon (UGA) (see FIG. 2, panel A). After mRNA editing, the UGA codon has been converted to UGI by deamination. UGI is read as UGG and the amino acid tryptophan is inserted.

EXEMPLIFICATION

Methods

A band-shift assay was used to test for Z-DNA binding activity. The probe was an oligomer of alternating deoxycytosine and deoxyguanosine which was modified by using the Klenow fragment of *E. coli* DNA polymerase I to incorporate $\alpha$-$^{32}$P labeled dGTP and d$^{5Br}$CTP (Herbert and Rich, (1993) *Nucl. Acids Res.* 21, 2669–2672). Binding specificity of proteins was determined by competition experiments using unlabeled DNA or RNA. Z-DNA specific interactions were demonstrated using either linear brominated polyd(CG) (Moller et al., (1984) *Biochemistry* 23, 54–62), or the plasmid pDHg16 which has a d(CG)13 insert in the Z-DNA conformation at bacterial superhelical density (Herbert and Rich, (1993) *Nucl. Acids Res.* 21, 2669–2672; Haniford and Pulleyblank, (1983) *J. Biomol. Struct. Dyn.* 1, 593–609).

Southwestern assays were performed using the Mini-Protean II system (Biorad, Melville, N.Y.). Proteins were heated at 70° C. in reducing sample buffer for 2 minutes, separated by SDS-PAGE electrophoresis in 7.5% resolving gel (Laemmli, (1970) *Nature* (London) 227, 680–685). They were then transferred from the gel to a 0.2µ reinforced nitrocellulose membrane (Biorad, Melville, N.Y.) in buffer (800 ml 1×Tris/glycine running buffer without SDS, 200 ml 100% methanol) at 500 mA for 75 minutes at 4° C. using a pre-frozen Bio-Ice cooling unit (Biorad, Melville, N.Y.). Colored molecular weight markers were used as specified by the supplier (Biorad, Melville, N.Y.). Membranes were blocked with 1% bovine serum albumin in Buffer I (PBS/ 0.1% Tween 20 and 5 mm DTT) (Sambrook et al., (1989) *Molecular Cloning: A Laboratory Manual* (Cold Spring Harbour Lab., Plainview, N.Y.), 2nd Ed.) for 60 minutes and then washed twice for 5 minutes in Buffer I. Before use, the radioactive probe was placed in 12 mM MgCl$_2$ for 15 minutes in a final volume of 0.25 ml to promote the formation of Z-DNA (Herbert and Rich, (1993) *Nucleic Acids Res.* 21, 2669–2672). Usually membranes were incubated in 5 ml of Buffer I, 10$^6$ cpm of probe(~5 ng), 20 µg of sheared salmon sperm DNA (5 prime-3 prime, Boulder, Colo.) and various other unlabeled DNA or RNA competitors as specified for 45 to 90 minutes. The membranes were then rinsed briefly in Buffer I three times (total time 5 minutes), dried and exposed to film.

Double-stranded RNA adenosine deaminase activity was assayed using Nuclease P1 and cellulose thin layer chromatography(TLC) as described (Bass and Weintraub, (1988) *Cell* 55, 1089–1098; O'Connell and Keller, (1994) *Proc. Natl. Acad. Sci. USA* 91, 10596–10600). The RNA probe was prepared from the 136 bp polylinker of pLITMUS 38 (NEB, Beverly, Mass.) which has T7 RNA polymerase promoters at either end, and gel purified. RNA was stored at –20° C. until use. Adenosine deaminase reactions were performed in a final volume of 50 µl with 1 femtomole of probe in 100 mM Tris-HCl(pH 7.4), 50 mM NaCl, 0.15 mg/ml tRNA, 0.1 mg/ml BSA, 5 mM DTT, either 5 mM EDTA or 10 mM MgCl$_2$ and 1–2 µl of Z-DNA affinity purified fraction. Reactions were stopped by addition of 50 ml of 0.2% SDS, and extracted with phenol/chloroform before precipitation with 0.1 volumes of (NaOAc(pH5.2)/ 2.5 volumes of EtOH). After a 70% EtOH wash, the pellets were dried under vacuum and resuspended in 10 µl of buffer (30 mM NaOAc(pH5.2), 0.1 mM ZnOAc) containing 1.5 µg of Nuclease P1 (Boehringer Mannheim, Indianapolis, Ind.). Digestion was performed at 55° C. for 1 hour. TLC was performed using cellulose plates as described (Bass and Weintraub, (1988) *Cell* 55, 1089–1098; O'Connell and Keller, (1994) *Proc. Natl. Acad. Sci. USA* 91, 10596–10600).

Following tailing of polyd(CG) with 5-(3-aminoallyl) 2'-deoxyuridine 5' triphosphate (Sigma Chemicals, A5910), DNA was biotinylated in NaTRICINE (pH8.8) with biotinamidocaproate N-hydroxysuccinimide ester (0.2 mg/ml) (Sigma Chemicals, B2643) which had been dissolved in dimethylsulfoxide(1 mg/ml). The polymer was stabilized in the Z-DNA conformation by bromination (Moller et al., (1984) *Biochemistry* 23, 54–62) and stored at –20° C. until used. To prepare the affinity matrix, 25 µg biotinylated Z-DNA was bound to 0.25 ml of Strepavidin Dynabeads M-280 (Dynal, Lake Success, N.Y.) and washed extensively in 10×PBS and PBS/0.1% NP40 before use. A similar strategy was used to prepare polyr(LC) columns except that T4 RNA ligase was used to introduce a primary amine into the polymer using N$^6$-(6 aminohexyl)adenosine 3',5'-diphosphate (Sigma A0394).

Lungs were collected from freshly killed chickens (Eastern Live Poultry; Boston, Mass.) and cooled on ice. The lungs in batches of 32 (approximately 200 g of tissue) were blended at top speed with a Waring Blender in Buffer II (10 mM Tris-HCl, 1 mM EDTA, 5 mM MgCl$_2$, 0.2 mM EGTA, 1 mM PMSF, 1 mM benzamidine.HCl, pH 8.0) at 4° C. for 3×45 seconds over 20 minutes; 2-mercaptoethanol (final concentration 5 mM) and potassium chloride (final concentration 100 mM) were then added. The mixture was then further blended at low speed for 4×5 seconds over 30 minutes, and then centrifuged at –4° C. for 30 minutes at 27,000×g.

The supernatant, which has a total cation concentration of approximately 150 mM and a volume of 750 ml, was carefully separated from the loose pellet and passed through a tight weave vegetable strainer to remove fatty sinew. 37 ml of buffer III (1.5M sucrose, 50 mM Tris-HCl, 50 mM KCl, 5 mM $MgCl_2$, 0.2 mM EGTA, 5 mM 2-mercaptoethanol, 1 mM AEBSF, 1 µM E64, pH 8.0) was added to this extract. 24 heat sealable; 39 ml centrifuge tubes (Seton Scientific) were prepared at 4° C. with a 10 ml sucrose step of buffer III, onto which the extract was layered. The tubes were then sealed and centrifuged at 40,000×g for 14 hours at 4° C. in a TFT50 type rotor (Dupont, Del.). The supernatant (extract and sucrose step) from each tube was carefully aspirated so as not to contaminate the pellet. The pellets from twelve tubes were then resuspended on ice in Buffer IV (50 mM Tris-HCl, 50 mM NaCl, 5 mM $MgCl_2$, 1 mM EDTA, 1 mM PMSF, 1 mM AEBSF, 1 µM E64, pH 8.0), which had been adjusted to 500 mM NaCl (final volume 11 ml), pooled and rocked at 4° C. until the solution cleared. 0.5 ml of 1M $MgCl_2$ was then added, and the suspension was centrifuged in a TH641 rotor (Dupont, Del.) at 36000 rpm for 20 hrs at 4° C. Supernatants (approximately 22 ml from each batch of 32 lungs) were either frozen at −20° C. until use or diluted to a final volume of 50 ml and loaded onto a 5 ml prepacked HiTrap heparin column (Pharmacia, Piscataway, N.J.) equilibriated in 50 mM NaHEPES (pH7.4), 200 mM NaCl, 1 mM EDTA, 1 mM DTT, 10% glycerol and a cocktail of protease inhibitors as follows: 5 mM sodium metabisulfite, 1.25 mM orthophenanthroline, 1 mM AEBSF, 250 µM PMSF, 250 µM benzamidine, 1 µM E64, and 0.5 µg/ml each of antipain, aprotinin, chymostatin, leupeptin, and pepstatin. Proteins were eluted with a 250 mM to 1M NaCl gradient: Z-DNA binding activity eluted at approximately 500 mM NaCl. Active fractions were then pooled, concentrated using a Centricon 100 (Amicon, Beverly, Mass.), diluted to give a final salt concentration of 50 mM and loaded onto a MonoQ column (Pharmacia, Piscataway, N.J.). The MonoQ column was run in 10 mM Tris-HCL buffer (pH 7.4), 1 mM EDTA, 1 mM DTT, 10% glycerol and the same cocktail of eleven protease inhibitors used for the previous column. A gradient was run from 50 mM to 500 mM NaCl to elute proteins. The activity eluted at approximately 220 mM NaCl and was further purified using a Z-DNA affinity column. Pooled fractions from the MonoQ column were diluted with an equal volume of Buffer IV and absorbed to washed beads pre-coated with Z-DNA for 1 hour in the presence of competitor (0.1 mg/ml polyr(A,U) Sigma P8662). The beads were washed twice with 1×PBS, 1 mM EDTA, 1 mM PMSF, 1 mM AEBSF, 1 µM E64, 0.1% NP40 then twice with Buffer V (50 mM TRICINE.HCl(pH 8.8), 150 mM NaCl, 0.1 mM EDTA, 1 mM AEBSF, 1 µM E64, 0.1% NP40). The activity was eluted in two steps using Buffer V/500 mM NaCl, then Buffer V/2M NaCl, made 50% in glycerol and stored at −20° C. Sequencing of peptides obtained by endoprotease Lys-C of nitrocellulose blots or by digestion of Coomassie stained protein bands was performed by conventional techniques.

Results

A previous report described a putative Z-DNA binding activity Zα (Herbert et al., (1993) *Proc. Natl. Acad. Sci. USA* 90, 3339–3342) that is present in chicken erythrocytes. It was observed that an activity with similar bandshift mobility and competition properties to Zα could be produced by trypsin treatment of lung extracts, which otherwise lacked Zα activity. It was further noted that the complex from which this activity could be derived was large enough to sediment through a 40% (w/w) sucrose step. This suggested that the Zα activity was a proteolytic product of a larger molecule and resulted in experimental efforts focusing on a band-shift activity present in a salt extract of the sucrose pellet. This activity produces a series of bands with the slowest electrophoretic mobility in the band-shift assay. The binding activity is Mg-dependent but ATP independent.

A protein of 140,000 molecular weight can be detected in partially pure extracts by probing a Western blot of an SDS-PAGE gel with a radioactively labeled Z-DNA probe. The band shift assay and the southwestern assay were used to monitor the purification of protein. Following heparin and MonoQ chromatography, it was observed that activities in both assays co-eluted from a Z-DNA affinity column. A silver stained gel of the fractions from a Z-DNA column showed that a 140,000 MW protein was the major component in these fractions. A minor component of 150,000 was also detectable. The amount of 140,000 MW protein detected in the silver stained gel correlates exactly with the activity detected in the bandshift assay and the southwestern assay. Binding of the probe by the protein in the southwestern assay was competed with linear polyd(C-G) stabilized in the Z-DNA conformation by chemical bromination but not by unmodified polyd(CG) in the B-DNA conformation. The 150,000 MW protein also bound the Z-DNA probe in the southwestern assay and is likely to be a modified form of the 140,000 MW protein.

The specificity of the protein bandshift assay was examined using unlabeled competitor. Competition experiments were also performed with pDHg16, a plasmid which has a d(CG)13 insert (Haniford and Pulleyblank, (1983) *J. Biomol. Struct. Dyn.* 1, 593–609). The plasmid was used at bacterial superhelical density, or after relaxation with calf thymus topoisomerase I. At bacterial superhelical density the insert is in the Z-DNA conformation (Herbert and Rich, (1993) *Nucleic Acids Res.* 21, 2669–2672; Haniford and Pulleyblank, (1983) *J. Biomol. Struct. Dyn.* 1, 593–609). Competition experiments were performed by titrating unlabeled plasmid in fivefold dilution steps. Maximum competition by pDHg16 is obtained when the plasmid was fully supercoiled and was diminished approximately 100-fold by relaxation. Bandshifts caused by binding of multiple proteins to the probe are competed more readily by the supercoiled plasmid than bandshifts caused by binding one or two protein molecules. The results are consistent with the activity being specific for d(CG)13 in the Z-DNA conformation. Furthermore, the result confirms that binding to the radioactively labeled probe is not dependent on or specific for bromination.

The bandshift activity was also examined for binding to r(CG)12, which has an A-RNA conformation (Tinoco et al., (1986) in *Structure and Dynamics of RNA*, eds. van Knippenberg, P. H. & Hilbers, C. W (Plenum Press, New York, N.Y.), pp55–68), by using competition with an unlabeled chemically synthesized oligoribonucleotide. This competition was compared to that of the chemically synthesized oligodeoxyribonucleotides d(5BrCG)5, d(5BrCG)22 and d(CG)22. Each unlabeled oligonucleotide was titrated in the bandshift reaction mix in tenfold dilution steps. Both brominated DNA oligomers were able to compete with radioactively labeled probe for the protein and abolish the bandshift. The 44-mer was approximately 100 times more efficient than the 10-mer. This may reflect co-operativity in protein binding, which is possible with the longer probe, or differences between the two oligonucleotides involving the kinetics of Z-DNA formation. In contrast, the unbrominated DNA oligomer d(CG)22, which does not adopt the Z-DNA conformation under the conditions used, was at least $10^4$ less efficient than d(5BrCG)22 in competing for the binding of protein to the labeled probe. Competition by Z-DNA forming brominated deoxynucleotides, but not by unmodified d(CG)22, and competition by Z-DNA containing supercoiled plasmid that diminishes on relaxation of the plasmid suggest that binding of protein to the probe is Z-DNA specific. When the RNA oligomer is used as a competitor, no competition is observed in the concentration range used. Instead, a slight but reproducible enhancement of binding was found. It is possible that the r(CG)12 causes a conformational change in the protein that enhances binding of Z-DNA. When longer double stranded RNA(dsRNA) polymers, such as polyr(A.U) and polyr(I.C) are used, the Z-DNA bandshift activity can be supershifted suggesting that A-RNA binds to a site separate from the putative Z-DNA binding site.

Peptide sequence obtained from endoproteinase Lys-C digestion of this protein show homology to published sequences of double-stranded RNA adenosine deaminase (dsrad) (table 1). The molecular weight predicted from the dsrad nucleic acid sequences is identical to that obtained for the protein purified here. Dsrad modifies adenosine to form inosine in regions of dsRNA. To confirm that the putative Z-DNA binding protein has this activity, fractions from a Z-DNA affinity column were tested. Enzyme activity co-elutes with the Z-DNA binding protein and this confirms that the purified protein is dsrad. Slight activity is found in the non-bound fraction in the absence of Z-DNA binding activity. This is consistent with the hypothesis that the putative Z-DNA binding region and dsRNA-binding/enzyme active site are on different domains of the protein. However both activities are inhibited by p-hydroxymecuriphenyl-sulfonic acid (Hough and Bass, B. L. (1994) *J. Biol. Chem.* 269, 9933–9939).

TABLE 1

Comparison of sequences obtained from peptides of the chicken 140,000 protein and that published for human and rat double stranded RNA adenosine deaminase (H-dsrd and R-dsrd respectively). Only differences between human and rat sequences are indicated. Identical residues are shwon by a vertical dash and conservative substitutions by a (+). Residues that could not be assigned in the peptide are indicated by ( ).

| peptide 1 | | LQAPYQINHPEVGRVSVYD | | (SEQ ID NO. 1) |
|---|---|---|---|---|
| | | 1+  1+  +111  11111+11 | | |
| H-dsrd | 1095 | LRHPFIVNHPKVGRVSIYD | 1113 | (SEQ ID NO. 2) |
| R-dsrd | 1041 | --Y------------V-- | 1059 | (SEQ ID NO. 3) |
| peptide 2 | | K(    )RIFPAVTA | | (SEQ ID NO. 4) |
| | | 1        1+1111+1 | | |
| H-dsrd | 763 | KVGGRWFPAVCA | 774 | (SEQ ID NO. 5) |
| R-dsrd | 709 | -------------- | 720 | |

We claim:

1. An expressible genetic construct comprising the following elements which are fused to form a continuous reading frame:
   a) DNA encoding double-stranded RNA adenosine deaminase, or a portion thereof which retains Z-DNA binding specificity; and
   b) DNA encoding an effector function;
the fusion protein encoded by expressible the genetic construct being characterized by the ability to selectively modify gene expression.

2. The expressible genetic construct of claim 1 wherein selectivity is provided by placing the expressible genetic construct under the regulatory control of a tissue-specific promoter.

3. The expressible genetic construct of claim 1 wherein selectivity is provided by an inherent substrate specificity of the effector function.

4. The expressible genetic construct of claim 1 wherein the effector function is a nuclease activity.

5. The expressible genetic construct of claim 1 wherein the effector function is a protease activity.

6. The expressible genetic construct of claim 1 wherein the effector function is a protein modifying activity.

7. The expressible genetic construct of claim 6 wherein the protein modifying activity is a phosphorylative or dephosphorylative activity.

8. The expressible genetic construct of claim 1 wherein the effector function is an mRNA editing activity.

9. An expressible genetic construct comprising the following elements which are fused to form a continuous reading frame:
   a) DNA encoding double-stranded RNA adenosine deaminase, or a portion thereof which retains Z-DNA binding specificity; and
   b) DNA encoding a B-DNA binding domain, the B-DNA binding domain being characterized by the ability to bind to a transcribed region of a gene of interest; and
   c) DNA encoding an effector function.

10. The expressible genetic construct of claim 9 wherein the effector function is a nuclease activity.

11. The expressible genetic construct of claim 9 wherein the effector function is a protease activity.

12. The expressible genetic construct of claim 9 wherein the effector function is a protein modifying activity.

13. The expressible genetic construct of claim 12 wherein the protein modifying activity is a phosphorylative or dephosphorylative activity.

14. The expressible genetic construct of claim 9 wherein the effector function is an mRNA editing activity.

15. An expressible genetic construct comprising the following elements which are fused to form a continuous reading frame:
   a) DNA encoding double-stranded RNA adenosine deaminase, or a portion thereof which retains Z-DNA binding specificity; and
   b) DNA encoding a B-DNA binding domain from a protein, the binding of said protein to a specific site in genomic DNA functioning to enhance transcription of the gene of interest, the B-DNA binding domain being characterized by the ability to bind specifically, and with high affinity to the specific site in genomic DNA, and the inability to enhance transcription of the gene of interest.

16. The expressible genetic construct of claim 15 wherein the B-DNA binding domain is a promoter-binding factor.

17. The expressible genetic construct of claim 15 wherein the B-DNA binding domain is an enhancer-binding factor.

18. A method for specifically modifying the production of a predetermined protein, the method comprising:
   a) providing an expressible genetic construct comprising the following elements which are fused to form a continuous reading frame:
      i) DNA encoding double-stranded RNA adenosine deaminase, or a portion thereof which retains Z-DNA binding specificity; and
      ii) DNA encoding an effector function;
      the fusion protein encoded by expressible the genetic construct being characterized by the ability to selectively modify gene expression; and
   b) introducing the genetic construct of step a), or the fusion protein encoded by the construct, into a cell which expresses the gene encoding the predetermined protein, under physiological conditions.

19. The method of claim 18 wherein the fusion protein encoded by the construct is introduced into the cell which expresses the gene encoding the predetermined protein by attaching folate to the surface of the fusion protein and contacting the cell with the folate-bearing fusion protein.

20. The method of claim 18 wherein the genetic construct is introduced into the cell by transfection.

21. A method for specifically modifying the production of a predetermined protein, the method comprising:
   a) providing a genetic construct comprising the following elements which are fused to form a continuous reading frame:
      i) DNA encoding double-stranded RNA adenosine deaminase, or a portion thereof which retains Z-DNA binding specificity; and
      ii) DNA encoding a B-DNA binding domain specific for the gene encoding the predetermined protein; and
      iii) DNA encoding an effector function;
   b) introducing the genetic construct of step a), or the fusion protein encoded by the construct, into a cell which expresses the gene encoding the predetermined protein, under physiological conditions.

22. The method of claim 21 wherein the fusion protein encoded by the construct is introduced into the cell which expresses the gene encoding the predetermined protein by attaching folate to the surface of the fusion protein and contacting the cell with the folate-bearing fusion protein.

23. The method of claim 21 wherein the genetic construct is introduced into the cell by transfection.

24. A method for specifically modifying the production of a predetermined protein, the method comprising:
   a) providing a genetic construct comprising the following elements which are fused to form a continuous reading frame:
      i) DNA encoding double-stranded RNA adenosine deaminase, or a portion thereof which retains Z-DNA binding specificity; and
      ii) DNA encoding a B-DNA binding domain from a protein, the binding of said protein to a specific site in genomic DNA functioning to enhance transcription of the gene of interest, the B-DNA binding domain being characterized by the ability to bind specifically, and with high affinity to the specific site in genomic DNA, and the inability to enhance transcription of the gene of interest;
   b) introducing the genetic construct of step a), or the fusion protein encoded by the construct, into a cell which expresses the gene encoding the predetermined protein, under physiological conditions.

25. The method of claim 21 wherein the fusion protein encoded by the construct is introduced into the cell which expresses the gene encoding the predetermined protein by attaching folate to the surface of the fusion protein and contacting the cell with the folate-bearing fusion protein.

26. The method of claim 24 wherein the genetic construct is introduced into the cell by transfection.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Lys Gln Arg Pro Tyr Gln Ile Asn His Pro Glu Val Gly Arg Val Ser
 1               5                  10                  15
Val Tyr Asp
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Lys Arg His Pro Phe Ile Val Asn His Pro Lys Val Gly Arg Val Ser
 1               5                  10                  15
Ile Tyr Asp
```

(2) INFORMATION FOR SEQ ID NO:3:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

```
Lys Arg Tyr Pro Phe Ile Val Asn His Pro Lys Val Gly Arg Val Ser
 1               5                  10                  15
Val Tyr Asp
```

(2) INFORMATION FOR SEQ ID NO:4:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

```
Lys Xaa Xaa Xaa Arg Ile Phe Pro Ala Val Thr Ala
 1               5                  10
```

(2) INFORMATION FOR SEQ ID NO:5:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

```
Lys Val Gly Gly Arg Trp Phe Pro Ala Val Cys Ala
 1               5                  10
```